(12) United States Patent
Navarro et al.

(10) Patent No.: US 7,186,114 B2
(45) Date of Patent: Mar. 6, 2007

(54) SELF-LIGATING LINGUAL ORTHODONTIC BRACKET

(76) Inventors: Carlos F. Navarro, 4514 Cole #910, Dallas, TX (US) 75230; Marco A. Navarro, 4514 Cole Ave. Suite 910, Dallas, TX (US) 75205

( * ) Notice: Subject to any disclaimer, the term of this patent is extended or adjusted under 35 U.S.C. 154(b) by 203 days.

(21) Appl. No.: 10/812,812

(22) Filed: Mar. 30, 2004

(65) Prior Publication Data
US 2005/0221248 A1 Oct. 6, 2005

(51) Int. Cl.
*A61C 7/12* (2006.01)
(52) U.S. Cl. .................................................... 433/11
(58) Field of Classification Search ............ 433/8, 433/10, 11, 13
See application file for complete search history.

(56) References Cited

U.S. PATENT DOCUMENTS

| | | | | |
|---|---|---|---|---|
| 4,337,037 | A * | 6/1982 | Kurz | 433/8 |
| 5,586,882 | A * | 12/1996 | Hanson | 433/13 |
| 5,906,486 | A * | 5/1999 | Hanson | 433/11 |
| 6,264,468 | B1 * | 7/2001 | Takemoto | 433/8 |
| 6,368,105 | B1 * | 4/2002 | Voudouris et al. | 433/11 |
| 6,776,613 | B2 * | 8/2004 | Orikasa | 433/11 |
| 6,843,651 | B2 * | 1/2005 | Orikasa | 433/13 |
| 2004/0166458 | A1 * | 8/2004 | Opin et al. | 433/11 |
| 2005/0019719 | A1 | 1/2005 | Hanson | 433/10 |

OTHER PUBLICATIONS

Hatto Loidl, "Self-Ligating Lingual Brackets," Dr Med Dent, Orthodontic Products, 4 pages (includes magazine cover page), Feb. 2004.
J.R. Smith, et al., "Twelve Key Principles of Lingual Orthodontic Therapy," white paper, Ormco Corporation, 4 pages, Apr. 1985.
Unknown, "Lingual" brochure, Ormco Corporation, 6 pages, undated.
John R. Smith, et al., "Keys to Success in Lingual Therapy, Part 1," Journal of Clinical Orthodontics, vol. XX No. 4, 23 (includes magazine cover page), Apr. 1986.

(Continued)

*Primary Examiner*—Cris L. Rodriguez
*Assistant Examiner*—Patrick J. Kilkenny
(74) *Attorney, Agent, or Firm*—Baker Botts L.L.P.

(57) ABSTRACT

According to one embodiment, a self-ligating lingual orthodontic bracket includes a base, flanges extending from the base to define a slot, and a clip. The clip applies a force to an object to secure the wire within the slot in a self-ligating manner. The clip is adapted to be urged vertically toward the occlusal plane from a closed position to an open position to expose the slot to receive the wire, the clip being biased against the second flange when the clip is in the open position due to the applied force. The clip is adapted to be urged vertically away from the occlusal plane from the open position to the closed position to secure the wire within the slot, the clip being biased against the wire when the clip is in the closed position and the wire is secured within the slot due to the applied force.

20 Claims, 10 Drawing Sheets

OTHER PUBLICATIONS

C. Moody Alexander, et al., "Lingual Orthodontics A Status Report," Journal of Clinical Orthodontics, vol. XVI, No. 4, 9 pages (includes magazine cover), Apr. 1982.

Craven Kurz, et al., "Part 2 Research and Development," Lingual Orthodontics: A Status Report, Journal of Clinical Orthodontics, vol. XVI, No. 11, 6 pages, Nov. 1982.

Robert P. Scholz, et al., "Part 3 Indirect Bonding—Laboratory and Clinical Procedures," Lingual Orthodontics: A Status Report, Journal of Clinical Orthodontics, vol. XVI, No. 12, 8 pages, Dec. 1982.

John C. Gorman, et al, "Part 4 Diagnosis and Treatment Planning," Lingual Orthodontics: A Status Report, Journal of Clinical Orthodontics, vol. XVII, No. 1, 10 pages, Jan. 1983.

C. Moody Alexander, et al., "Part 5 Lingual Mechanotherapy," Lingual Orthodontics: A Status Report, Journal of Clinical Orthodontics, vol. XVII, No. 2, 17 pages, Feb. 1983.

C. Moody Alexander, et al., "Part 6, Patient and Practice Management," Lingual Orthodontics: A Status Report, Journal of Clinical Orthodontics, vol. XVII No. 4, 7 pages, Apr. 1983.

Craven Kurz, et al., "Part 7A, Case Reports—Nonextraction, Consolidation," Lingual Orthodontics: A Status Report, Journal of Clinical Orthodontics, vol. XVII, No. 5, 12 pages, May 1983.

Unknown, "Ovation Systems," GAC International, Inc., Catalog 11, 18 pages (includes cover page, Introduction page, Table of Contents page), Copyright 2001.

* cited by examiner

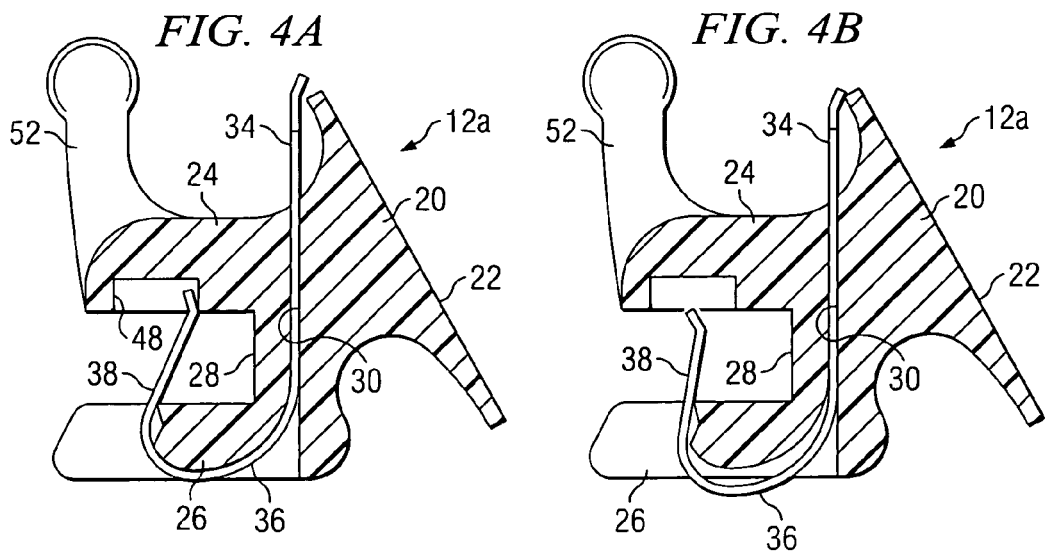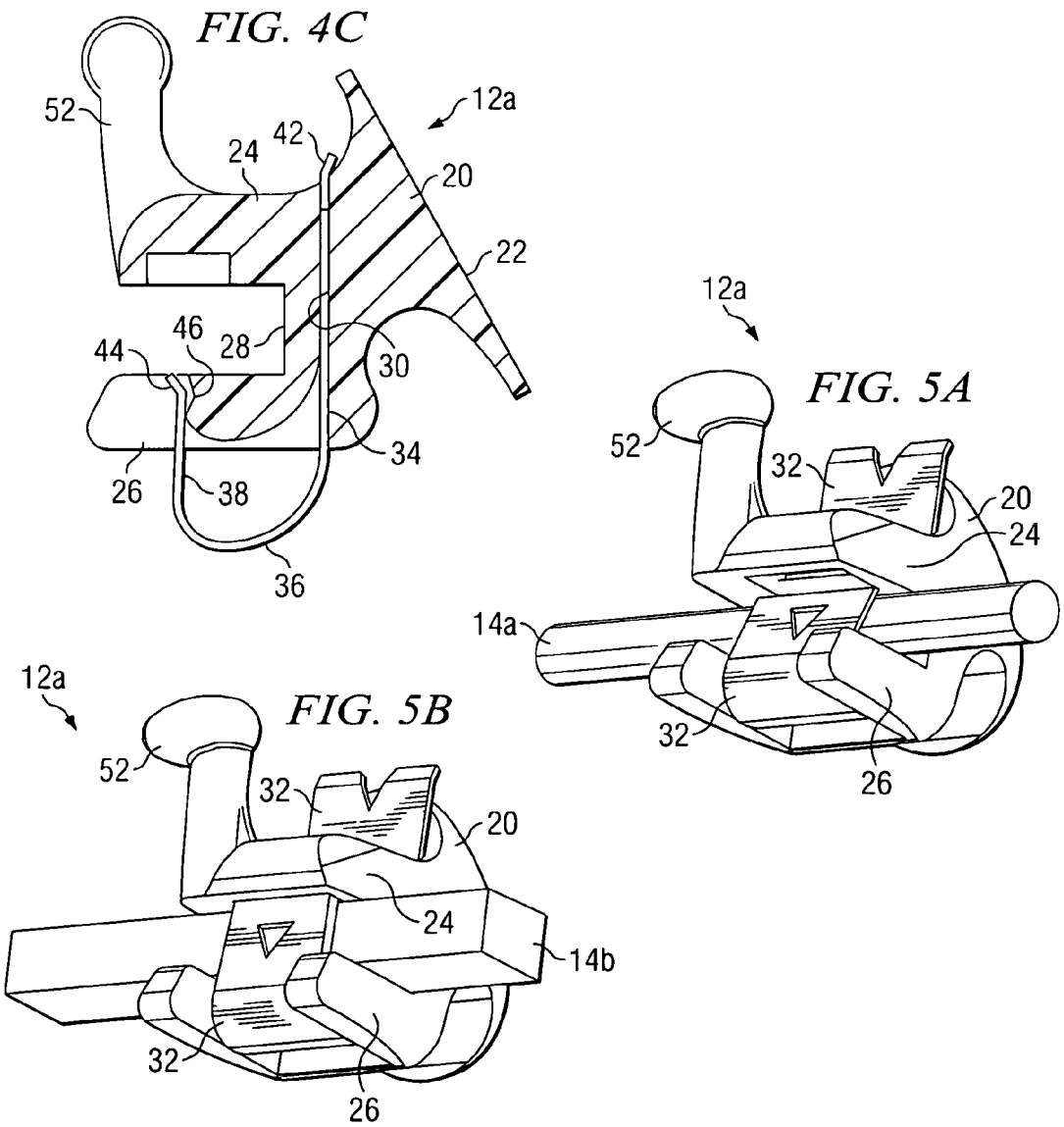

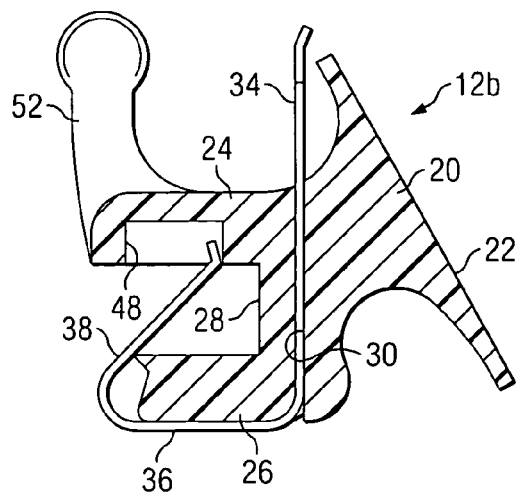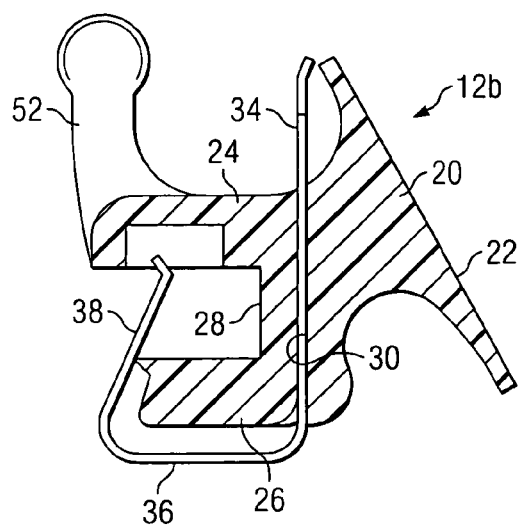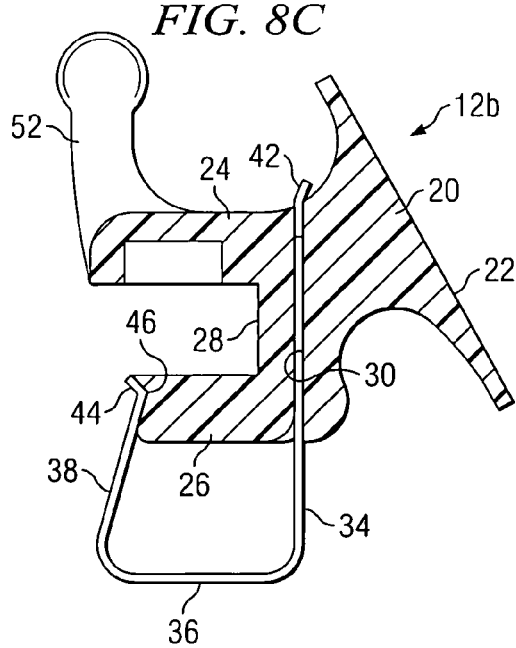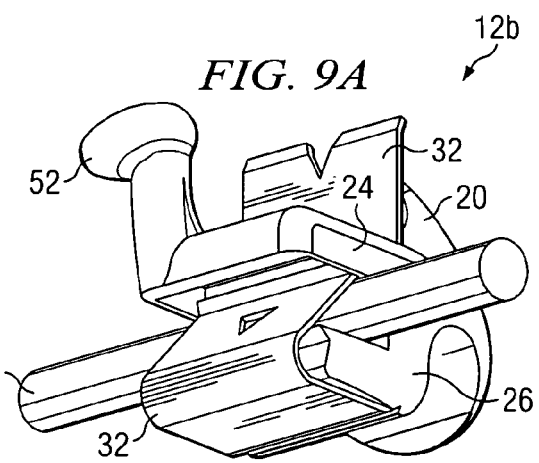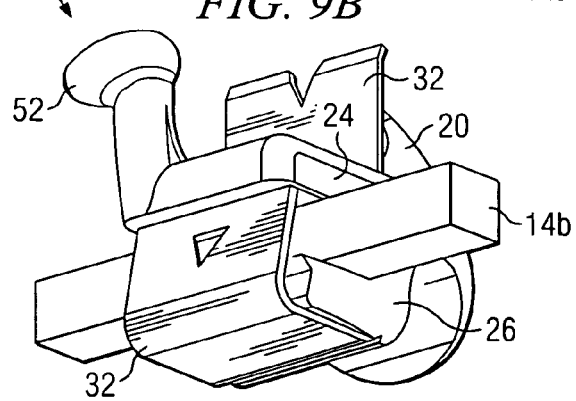

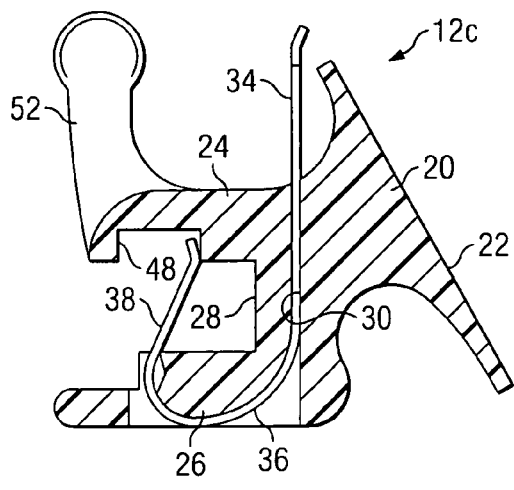
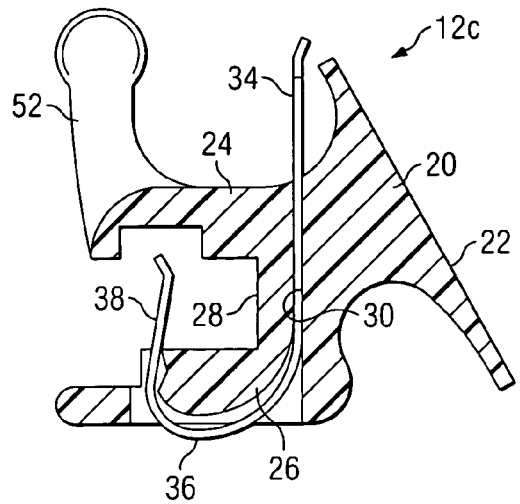
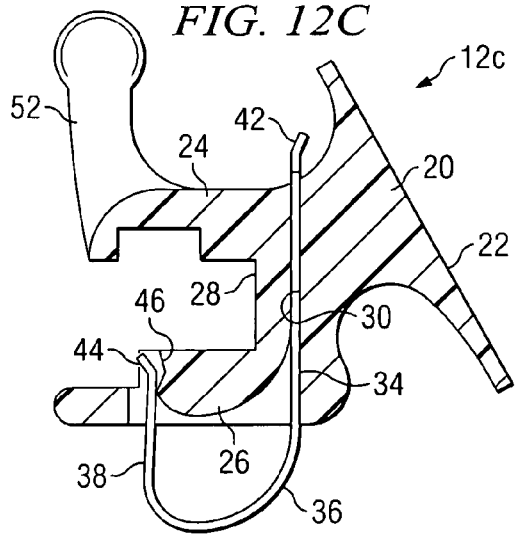
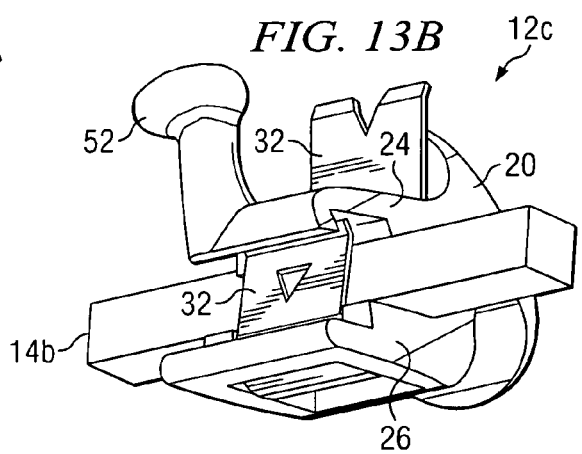
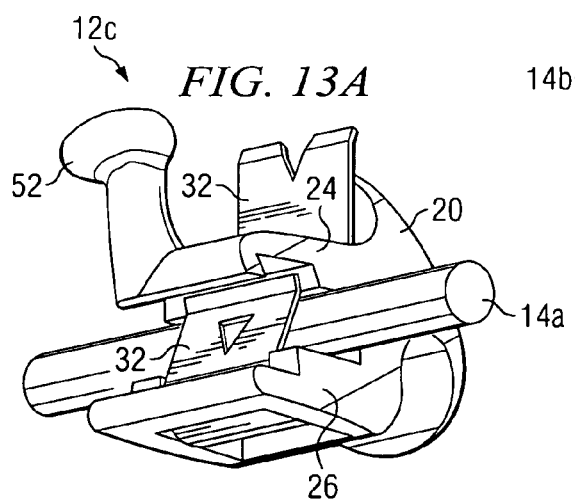

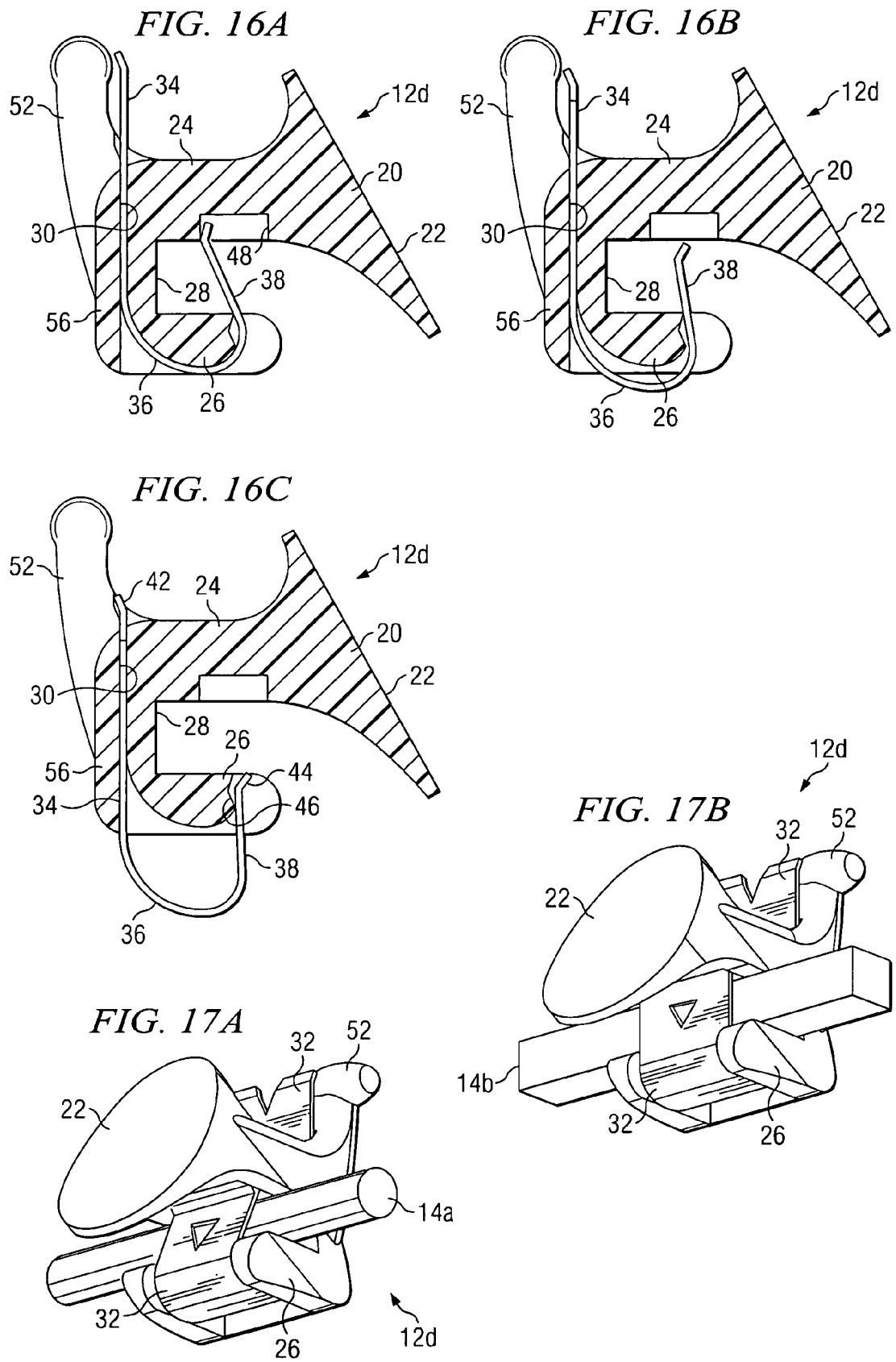

SELF-LIGATING LINGUAL ORTHODONTIC BRACKET

TECHNICAL FIELD

This invention relates generally to orthodontics and in particular to a self-ligating lingual orthodontic bracket.

BACKGROUND

Many people experience cosmetic, medical, and other problems resulting from improper positioning of the teeth and associated oral structures. Through the use of orthodontic brackets affixed to the teeth and coupled to one another with orthodontic wire, the teeth may be forced into proper position over an extended period of time. Labial orthodontic brackets are affixed to the labial or outside surface of the teeth. The use of labial brackets is common and their mechanism of operation to correct improper positioning of the teeth and associated oral structures is well understood by most orthodontic professionals. Certain previous labial brackets are self-ligating, meaning that a bracket includes a clip or other mechanism to secure the orthodontic wire in place against the lingual surface of the bracket. In contrast to labial brackets, lingual orthodontic brackets are affixed to the lingual or inside surface of the teeth. The use of lingual brackets is less common and, accordingly, their mechanism of operation to correct improper positioning of the teeth and associated oral structures is less well understood by most orthodontic professionals.

SUMMARY OF THE INVENTION

The orthodontic brackets of the present invention may reduce or eliminate problems and disadvantages associated with previous orthodontic brackets.

According to one embodiment, a self-ligating lingual orthodontic bracket is provided. The bracket includes a base comprising a base surface adapted for coupling to a lingual surface of a tooth in a person's arch. A first flange extends generally horizontally from the base in a generally lingual direction. A second flange extends generally horizontally from the base in a generally lingual direction, the second flange separated from the first flange generally vertically toward the person's occlusal plane to define a generally transverse wire slot that is exposed on a lingual side of the bracket and adapted to receive an orthodontic wire inserted into the wire slot from the lingual side of the bracket. A clip slot is formed generally vertically through the bracket. A flexible retaining clip is adapted to secure the orthodontic wire within the wire slot in a self-ligating manner. The retaining clip comprises a first portion positioned generally vertically and adapted to move generally vertically within the clip slot toward or away from the occlusal plane, a second portion extending generally horizontally from the first portion in a generally lingual direction about at least a central portion of the second flange, and a third portion extending generally vertically from the second portion in a direction generally away from the occlusal plane about at least the central portion of the second flange. The retaining clip is adapted to apply a resilient force to an object positioned between the first and third portions. The retaining clip is also adapted to be urged generally vertically toward the occlusal plane from a closed position to an open position to expose the wire slot to receive the orthodontic wire, the third portion being biased against at least the central portion of the second flange when the retaining clip is in the open position due to the applied resilient force. The retaining clip is also adapted to be urged generally vertically away from the occlusal plane from the open position to the closed position to secure the orthodontic wire within the wire slot, the third portion being biased against the orthodontic wire when the retaining clip is in the closed position and the orthodontic wire is secured within the wire slot due to the applied resilient force.

Particular embodiments of the present invention may provide one or more technical advantages. In particular embodiments, the present invention overcomes difficulties and challenges associated with providing an orthodontic bracket that is self-ligating and also adapted for use inside a person's mouth (i.e. is a lingual bracket). For example, in certain embodiments, the self-ligating lingual brackets must integrate an orthodontic prescription appropriate for self-ligating lingual brackets, including a particular combination of torque, angulation, thickness, or other parameters, that is appropriate for self-ligating lingual brackets and may be substantially different from an orthodontic prescription appropriate for self-ligating labial brackets. As another example, in contrast to self-ligating labial brackets in which the orthodontic wire applies correcting forces against the lingual brackets toward the labial surfaces of the teeth, in certain embodiments the retaining clips and associated structures of the self-ligating lingual brackets must be adapted to accommodate correcting forces that are applied against the retaining clips away from the lingual surfaces of the teeth and may also be stronger than the correcting forces applied in the case of self-ligating labial brackets. As another example, in contrast to self-ligating labial brackets in which retaining clips may be readily accessed from outside the mouth for inserting, securing, and removing the orthodontic wire, in certain embodiments the retaining clips and associated structures of the self-ligating lingual brackets must facilitate access from inside the mouth for inserting, securing, and removing the orthodontic wire. Self-ligating lingual brackets according to certain embodiments of the present invention represent a significant technical advance over the prior art.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

For a more complete understanding of the present invention and advantages thereof, reference is now made to the following description taken in conjunction with the accompanying drawings, in which:

FIGS. 4A–4C illustrate side views of the first example bracket showing movement of an example active clip;

FIGS. 5A–5B illustrate perspective views of the first example bracket securing example orthodontic wires;

FIGS. 8A–8C illustrate side views of the second example bracket showing movement of an example active clip;

FIGS. 9A–9B illustrate perspective views of the second example bracket securing example orthodontic wires;

FIGS. 12A–12C illustrate side views of the third example bracket showing movement of an example active clip;

FIGS. 13A–13B illustrate perspective views of the third example bracket securing example orthodontic wires;

FIGS. 16A–16C illustrate side views of the fourth example bracket showing movement of an example active clip;

FIGS. 17A–17B illustrate perspective views of the fourth example bracket securing example orthodontic wires.

DESCRIPTION OF EXAMPLE EMBODIMENTS

Figure 1:
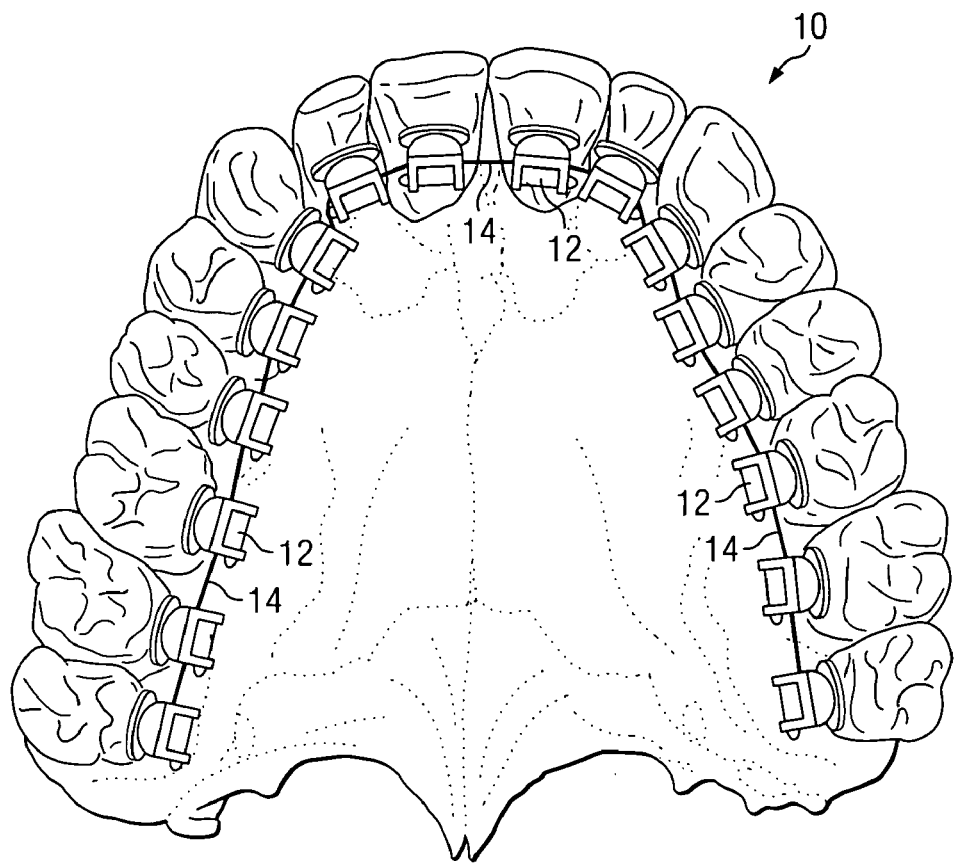
FIG. 1 illustrates a bottom view of a person's upper arch with example self-ligating lingual orthodontic brackets affixed to the user's upper teeth.

FIG. 1 illustrates a bottom view of a person's upper arch 10 with example self-ligating lingual orthodontic brackets 12 affixed to the upper teeth. For example, brackets 12 may be affixed to the upper teeth using a conventional indirect bonding technique or in any other suitable manner. Although upper arch 10 is illustrated with substantially identical brackets 12 affixed to all of the upper teeth, brackets 12 may be affixed to any two or more of the upper teeth, brackets 12 may be affixed to any two or more of lower teeth instead or in addition to two or more of the upper teeth, and a bracket 12 affixed to a tooth may be the same as or different than a bracket 12 affixed to another tooth in configuration, size, or both. As one example, brackets 12 affixed to central teeth may be different in both configuration and size than brackets 12 affixed to cuspids, bicuspids, or molars. As another example, a bracket 12 affixed to an upper tooth may be larger than a bracket 12 affixed to an opposing lower tooth.

Brackets 12 are coupled to one another using a suitable orthodontic wire 14. Orthodontic wire 14 may be formed from stainless steel, a nickel-titanium alloy, or any other suitable material, may have an ideal arch shape known to those of ordinary skill in the art or any other suitable shape, and may have a circular cross-section, a rectangular cross-section, or any other suitable cross-section. In certain embodiments, orthodontic wire 14 having a circular cross-section may be more desirable during the early stages of treatment, while orthodontic wire 14 having a rectangular cross-section may be more desirable during the later stages of treatment. In general, brackets 12 and orthodontic wire 14 cooperate to apply substantially continuous force to the teeth to gradually correct improper positioning of the teeth.

Figure 2:
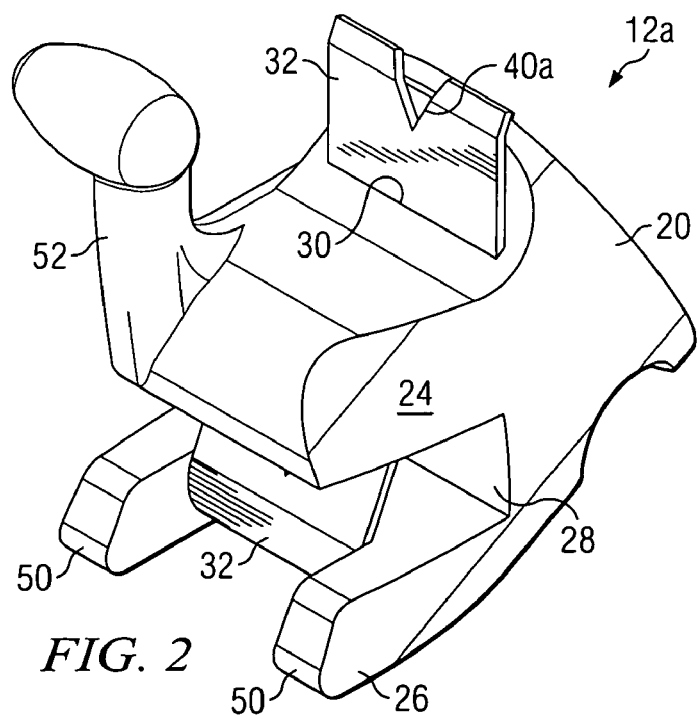
FIG. 2 illustrates a perspective view of a first example self-ligating lingual orthodontic bracket.
Figure 3A:
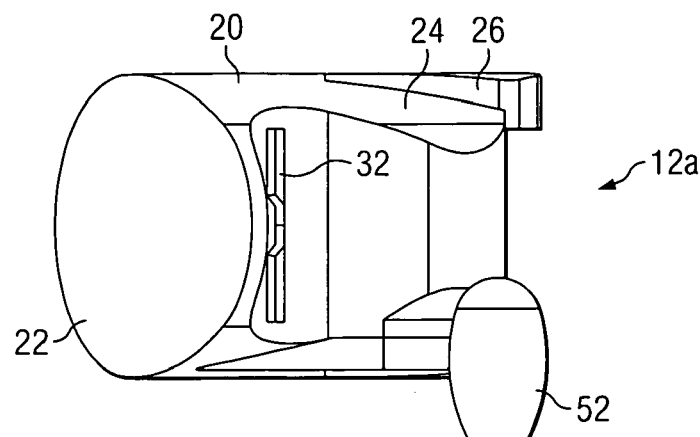
FIGS. 3A–3C illustrate top, side, and rear views of the first example bracket.
Figure 3C:
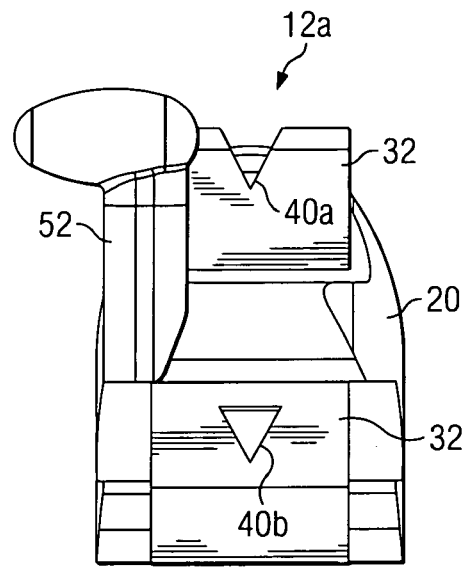
Figure 3B:
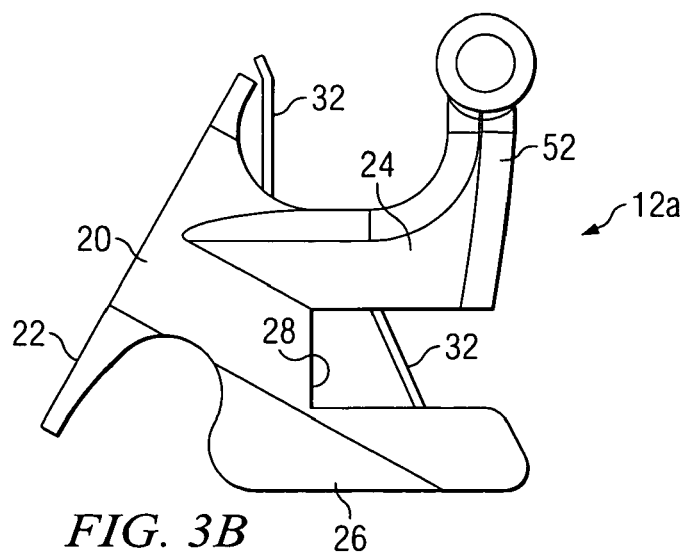

FIGS. 2–5 illustrate a first example self-ligating lingual orthodontic bracket 12a. In particular: FIG. 2 illustrates a perspective view of bracket 12a; FIGS. 3A–3C illustrate top, side, and rear views of bracket 12a; FIGS. 4A–4C illustrate side views of bracket 12a showing an example retaining clip 16 in closed, intermediate, and open positions; and FIGS. 5A–5B illustrate perspective views of bracket 12a securing orthodontic wires 14a and 14b having circular and rectangular cross-sections. As just an example, bracket 12a may be affixed to an upper central tooth and may be large, relative to other brackets 12, in light of the large size of the upper central teeth, relative to other upper and lower teeth.

Bracket 12a includes a base 20 comprising a base surface 22 adapted for coupling to a lingual surface of a tooth in arch 10. A first flange 24 and a second flange 26 extend generally horizontally from base 20 in a generally lingual direction (i.e. away from the tooth). First flange 24 and second flange 26 are separated from one another generally vertically in the direction of the person's occlusal plane to define a generally transverse wire slot 28 that is exposed on a lingual side of bracket 12a (i.e. the side away from the tooth) and is adapted to receive an orthodontic wire 14 inserted into wire slot 28 from the lingual side of the bracket 12a. A clip slot 30 is formed generally vertically through bracket 12a and is adapted to receive a retaining clip 32 that secures orthodontic wire 14 within wire slot 28 in a self-ligating manner (i.e. without requiring external mechanisms such as elastomers).

In certain embodiments, as illustrated in FIGS. 4A–4C, retaining clip 32 includes a first portion 34 positioned generally vertically and adapted to move generally vertically within clip slot 30 toward or away from the occlusal plane, a second portion 36 extending generally horizontally from first portion 34 in a generally lingual direction about at least a central portion of second flange 26, and a third portion 38 extending generally vertically from second portion 36 in a direction generally away from the occlusal plane about at least the central portion of second flange 26. Portions 34, 36, and 38 of retaining clip 32 may be integral or may include separate pieces of material coupled in any suitable manner. Portions 34, 36, and 38 may combine to provide retaining clip 32 having any suitable shape. For example, second portion 36 may extend generally horizontally from first portion 34 in a gradual curve as shown, at a sharp angle, or in any other appropriate manner. Similarly, for example, third portion 38 may extend generally vertically from second portion 36 in a gradual curve as shown, at a sharp angle, or in any other appropriate manner.

Retaining clip 32 may be resilient in that when first portion 34 is secured and third portion 38 is forced away from first portion 34 from an original position to an expanded position, the material of retaining clip 32 seeks to resiliently return third portion 38 from the expanded position to the original position. In other words, retaining clip 32 is adapted to apply a resilient force to an object of sufficient size that is positioned between first portion 34 and third portion 38. Thus, when first portion 34 is positioned in clip slot 30, orthodontic wire 14 is inserted in wire slot 28, and the presence of orthodontic wire 14 forces third portion 38 away from first portion 34 in the generally lingual direction, third portion 38 is biased against orthodontic wire 14 to secure orthodontic wire 14 within wire slot 28.

In operation of retaining clip 32, beginning in the closed position, retaining clip 32 is urged generally vertically toward the occlusal plane from the closed position as illustrated in FIG. 4A, through the intermediate position as illustrated in FIG. 4B, to the open position as illustrated in FIG. 4C to expose wire slot 28 to receive orthodontic wire 14. For example, where the tooth is an upper tooth in upper arch 10, retaining clip 32 is urged generally down from the closed position to the open position. Retaining clip 32 may be urged from the closed position to the open position in any suitable manner. As illustrated in FIGS. 5A–5B, at least one of first portion 34 and third portion 38 of retaining clip 32 may include a notch 40 adapted to receive a tool for urging retaining clip 32 toward the occlusal plane from the closed position to the open position. Although notches 40 are shown for example as being triangular, a notch 40 may have any suitable shape and may be open (like example notch 40*a*) or closed (like example notch 40*b*) in the direction generally away from the occlusal plane, according to particular needs.

In certain embodiments, as illustrated in FIG. 4C, free end 42 of first portion 34 of retaining clip 32 extends generally vertically from clip slot 30 in a direction generally away from the occlusal plane and may include an angle adapted to contact bracket 12*a* to limit movement of retaining clip 32 toward the occlusal plane as retaining clip 32 is urged from the closed position to the open position. In certain embodiments, also as illustrated in FIG. 4C, free end 44 of third portion 38 of retaining clip 32 is biased against at least the central portion of second flange 26 when retaining clip 32 is in the open position due to the applied resilient force. The central portion of second flange 26 may include a detent 46 adapted to receive free end 44 of third portion 38 of retaining clip 32 when retaining clip 32 is in the open position to help prevent unintentional movement of retaining clip 32 away from the occlusal plane. Free end 44 may be angled or otherwise shaped to help prevent free end 44 from snagging within detent 46 or on orthodontic wire 14 as retaining clip 32 is urged away from the occlusal plane.

In operation of retaining clip 32, beginning in the open position, retaining clip 32 is urged generally vertically away from the occlusal plane from the open position as illustrated in FIG. 4C, through the intermediate position as illustrated in FIG. 4B, to the closed position as illustrated in FIG. 4A to secure orthodontic wire 14 within wire slot 28. For example, where the tooth is an upper tooth in upper arch 10, retaining clip 32 is adapted to be urged generally up from the open position to the closed position. Retaining clip 32 may be urged from the open position to the closed position in any suitable manner. As one example, pressure may be applied to second portion 36 of retaining clip 32 in the direction generally away from the occlusal plane. As another example, a notch 40 may be diamond shaped or otherwise adapted to receive a tool for urging retaining clip 32 either toward or away from the occlusal plane.

In certain embodiments, as illustrated in FIG. 4A, second portion 36 of retaining clip 32 is adapted to contact the central portion of second flange 26 to limit movement of retaining clip 32 away from the occlusal plane as he retaining clip 32 is urged from the open position to the closed position. As illustrated in FIGS. 5A–5B, third portion 38 of retaining clip 32 is biased against orthodontic wire 14 when retaining clip 32 is in the closed position and orthodontic wire 14 is secured within wire slot 28 due to the applied resilient force. In certain embodiments, as illustrated in FIG. 4A, first flange 24 may include a recess 48 adapted to receive free end 44 of third portion 38 of retaining clip 32 when retaining clip 32 is in the closed position to limit movement of free end 44 in a generally lingual direction to help prevent orthodontic wire 14 from escaping from wire slot 28 and, as a result, jeopardizing the ability of bracket 12*a* to secure orthodontic wire 14.

In certain embodiments, as illustrated in FIG. 2, second flange 26 includes mesial and distal arms 50 defining a central gap through which third portion 38 of retaining clip 32 moves about the central portion of second flange 26. In these embodiments, third portion 38 of retaining clip 32 covers substantially all of the lingual surface of the central portion of second flange 26 and the lingual surface of third portion 38 of retaining clip 32 is entirely exposed. In certain embodiments, second flange 26 provides a bite plate adapted to contact an occlusal surface of an opposing tooth in the person's opposing arch 10 to limit movement of the tooth to which bracket 12*a* is affixed toward the opposing tooth. In certain embodiments, bracket 12*a* includes a hook 52 extending from a mesial or distal side of first flange 24 in a direction generally away from the occlusal plane. Hook 52 may include a ball-shaped or other free end adapted to engage with a rubberband or other elastomer operable to pull bracket 12*a* in a generally transverse direction toward an adjacent bracket 12.

Figure 6:
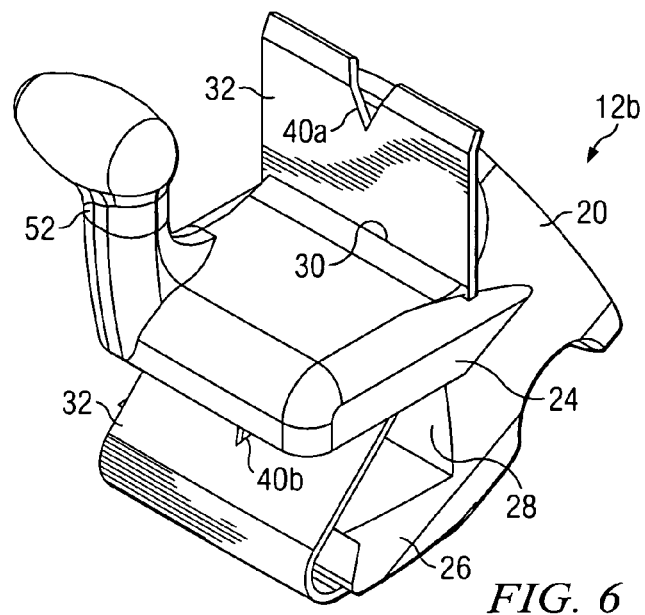
FIG. 6 illustrates a perspective view of a second example self-ligating lingual orthodontic bracket.
Figure 7A:
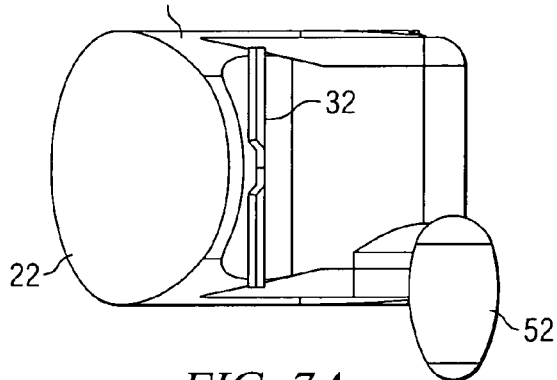
FIGS. 7A–7C illustrate top, side, and rear views of the second example bracket.
Figure 7B:
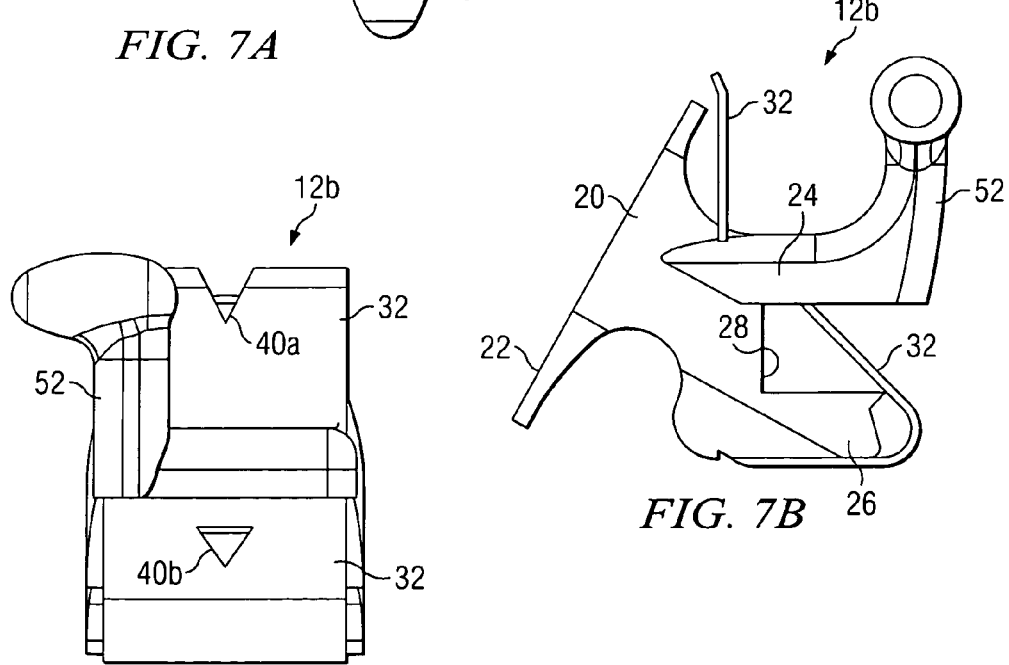
Figure 7C:
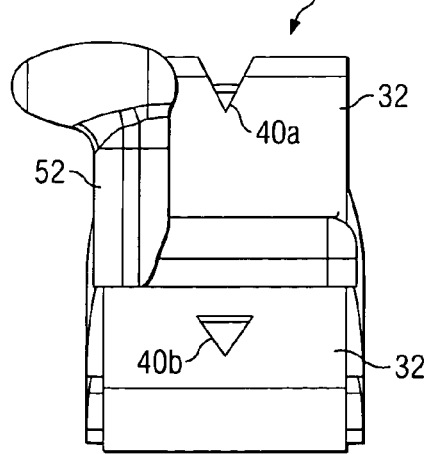

FIGS. 6–9 illustrate a second example self-ligating lingual orthodontic bracket 12*b*. In particular: FIG. 6 illustrates a perspective view of bracket 12*b*; FIGS. 7A–7C illustrate top, side, and rear views of bracket 12*b*; FIGS. 8A–8C illustrate side views of bracket 12*b* showing an example retaining clip 16 in closed, intermediate, and open positions; and FIGS. 9A–9B illustrate perspective views of bracket 12*b* securing orthodontic wires 14*a* and 14*b* having circular and rectangular cross-sections. As just an example, bracket 12*b* may be affixed to a lower central tooth and may be smaller than bracket 12*a* in light of the smaller size of the lower central teeth compared to the upper central teeth.

The features and operation of bracket 12*b* may be the same or substantially similar to the features and operation of bracket 12*a* described above with reference to FIGS. 2–5. In certain embodiments, rather than second flange 26 including arms 50 defining a central gap through which third portion 38 of retaining clip 32 moves about the central portion of second flange 26 and third portion 38 of retaining clip 32 covering substantially all of the lingual surface of the central portion of second flange 26, as described above for bracket 12*a*, in this case second flange 26 is continuous between its mesial and distal sides and third portion 38 of retaining clip 32 covers substantially all of the lingual surface of second flange 26 between its mesial and distal sides. Those skilled in the art will recognize that one or more other differences between bracket 12*b* and bracket 12*a* may be present without departing from the intended scope of the invention.

Figure 10:
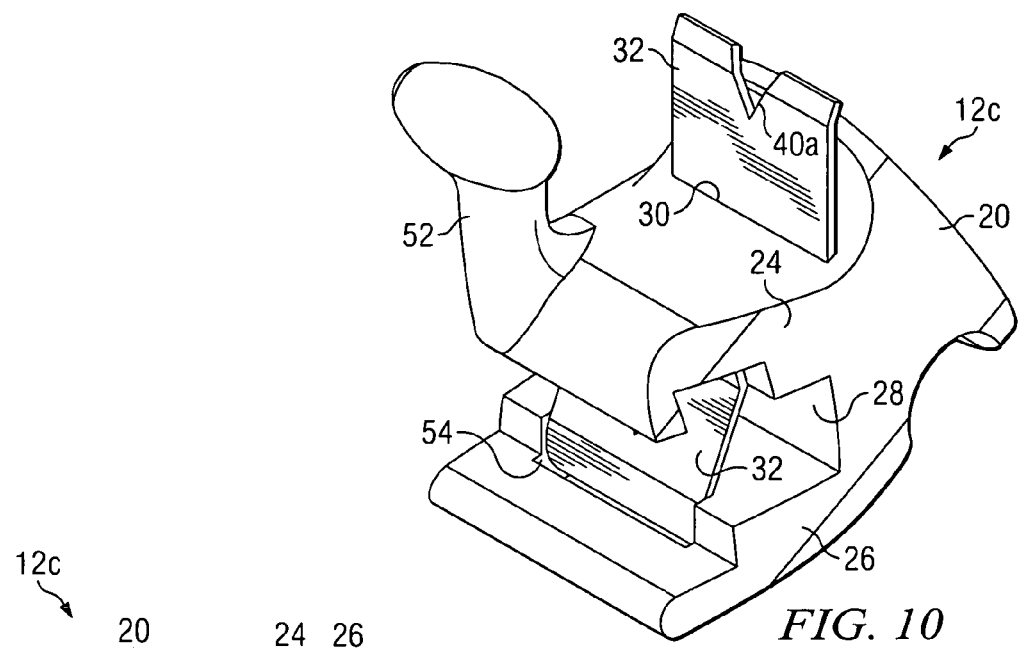
FIG. 10 illustrates a perspective view of a third example self-ligating lingual orthodontic bracket.
Figure 11A:
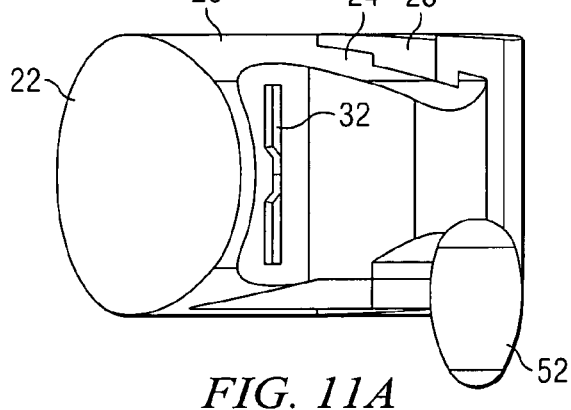
FIGS. 11A–11C illustrate top, side, and rear views of the third example bracket.
Figure 11B:
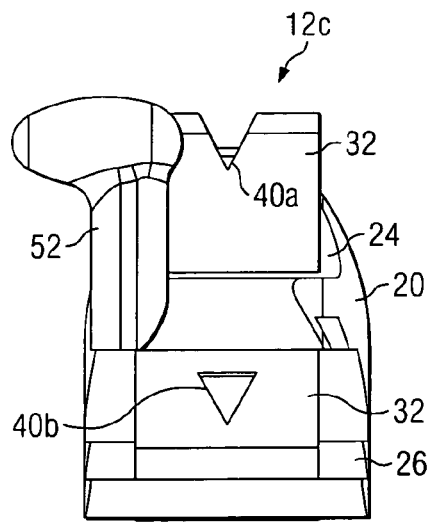
Figure 11C:
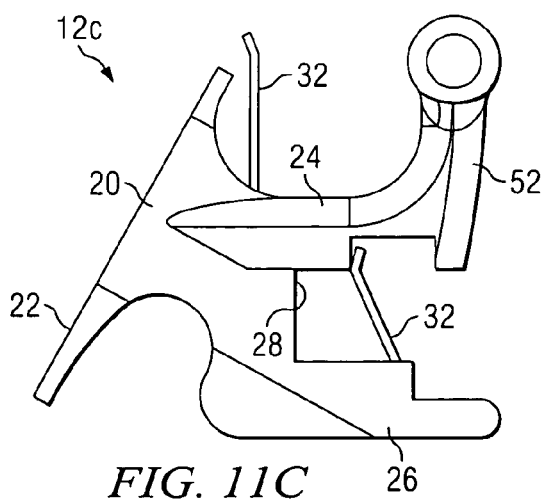

FIGS. 10–13 illustrate a third example self-ligating lingual orthodontic bracket 12*c*. In particular: FIG. 10 illustrates a perspective view of bracket 12*c*; FIGS. 11A–11C illustrate top, side, and rear views of bracket 12*c*; FIGS. 12A–12C illustrate side views of bracket 12*c* showing an example retaining clip 16 in closed, intermediate, and open positions; and FIGS. 13A–13B illustrate perspective views of bracket 12*c* securing orthodontic wires 14*a* and 14*b* having circular and rectangular cross-sections. As just an example, bracket 12*c* may be affixed to a lower central tooth and may be smaller than bracket 12*a* in light of the smaller size of the lower central teeth compared to the upper central teeth.

The features and operation of bracket 12*c* may be the same or substantially similar to the features and operation of bracket 12*a* described above with reference to FIGS. 2–5. In certain embodiments, rather than the lingual surface of third portion 38 of retaining clip 32 being entirely exposed, as described above for bracket 12*a*, in this case second flange 26 extends in the lingual direction past first flange 24 to provide an extended bite plate and second flange 26 includes a central slot 54 through which third portion 38 of retaining clip 32 moves about the central portion of second flange 26. Those skilled in the art will recognize that one or more other differences between bracket 12*c* and bracket 12*a* may be present without departing from the intended scope of the invention.

Figure 14:
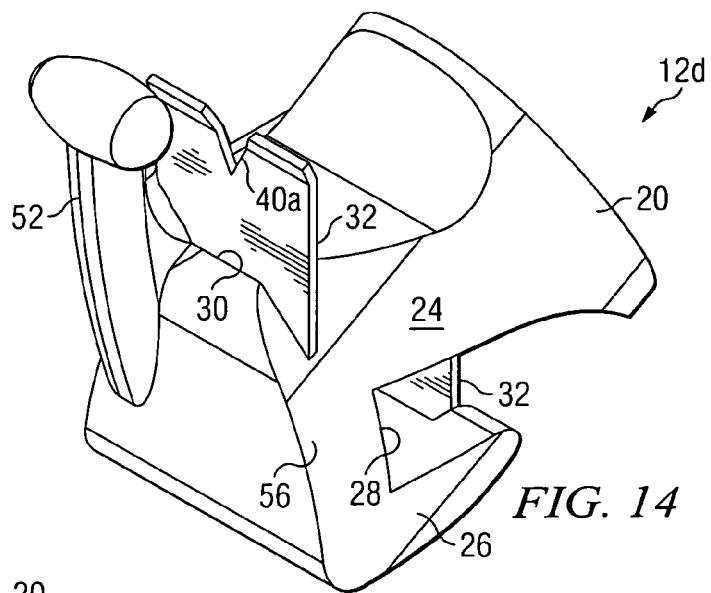
FIG. 14 illustrates a perspective view of a fourth example self-ligating lingual orthodontic bracket.
Figure 15A:
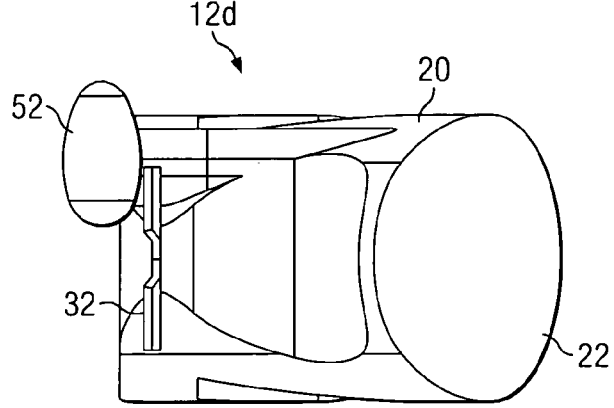
FIGS. 15A–15C illustrate top, side, and rear views of the fourth example bracket.
Figure 15B:
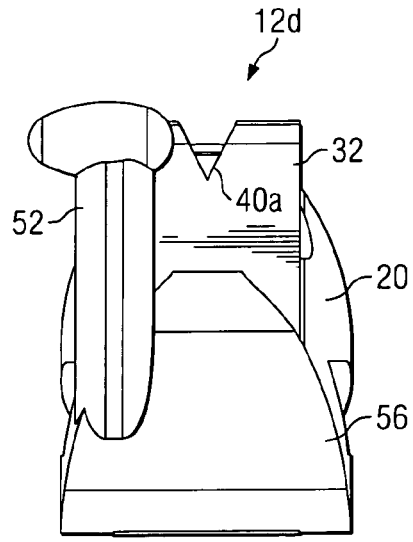
Figure 15C:
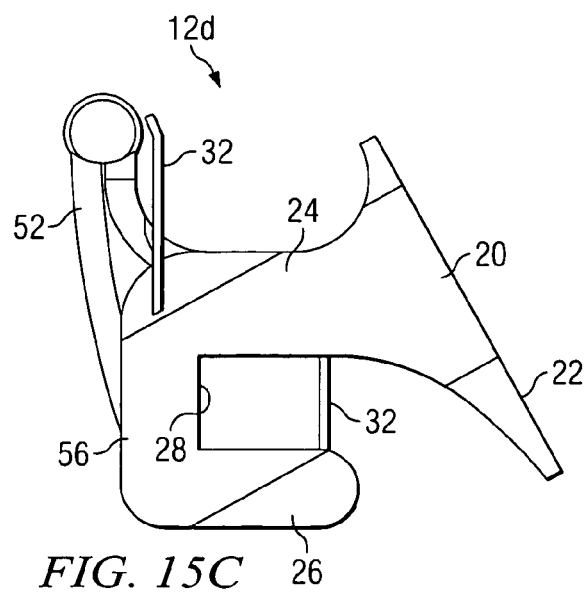

FIGS. 14–17 illustrate a fourth example self-ligating lingual orthodontic bracket 12*d*. In particular: FIG. 14 illustrates a perspective view of bracket 12*d*; FIGS.

15A–15C illustrate top, side, and rear views of bracket 12*d*; FIGS. 16A–16C illustrate side views of bracket 12*d* showing an example retaining clip 16 in closed, intermediate, and open positions; and FIGS. 17A–17B illustrate perspective views of bracket 12*d* securing orthodontic wires 14*a* and 14*b* having circular and rectangular cross-sections. As just an example, bracket 12*d* may be affixed to an upper central tooth and may be large, relative to other brackets 12, in light of the large size of the upper central teeth, relative to other upper and lower teeth.

Certain features and operation of bracket 12*d* may be the same or substantially similar to the features and operation of bracket 12*a* described above with reference to FIGS. 2–5. However, certain other features and operation of bracket 12*d* are essentially reversed from those of bracket 12*a*. In certain embodiments, rather than first flange 24 and second flange 26 extending generally horizontally from base 20 in a generally lingual direction, as described above for bracket 12*a*, in this case first flange 24 extends generally horizontally from base 20 in a generally lingual direction, a third flange 56 extends generally vertically from first flange 24 in a direction generally toward the occlusal plane, second flange 26 extends generally horizontally from third flange 56 in a generally labial direction (i.e. toward the tooth), and wire slot 28 is adapted to receive orthodontic wire 14 inserted into wire slot 28 first in a direction generally away from the occlusal plane to clear second flange 26 and then in a generally lingual direction to seat orthodontic wire 14 in wire slot 28. In these embodiments, the orientation of retaining clip 32 is modified accordingly. Those skilled in the art will recognize that one or more other differences between bracket 12*c* and bracket 12*a* may be present without departing from the intended scope of the invention. In certain embodiments, use of "reverse" brackets 12*d* allows the teeth to be moved more easily and thus the positioning of the teeth to be corrected more easily than with "forward" brackets 12*a*–12*c*.

Figure 18:
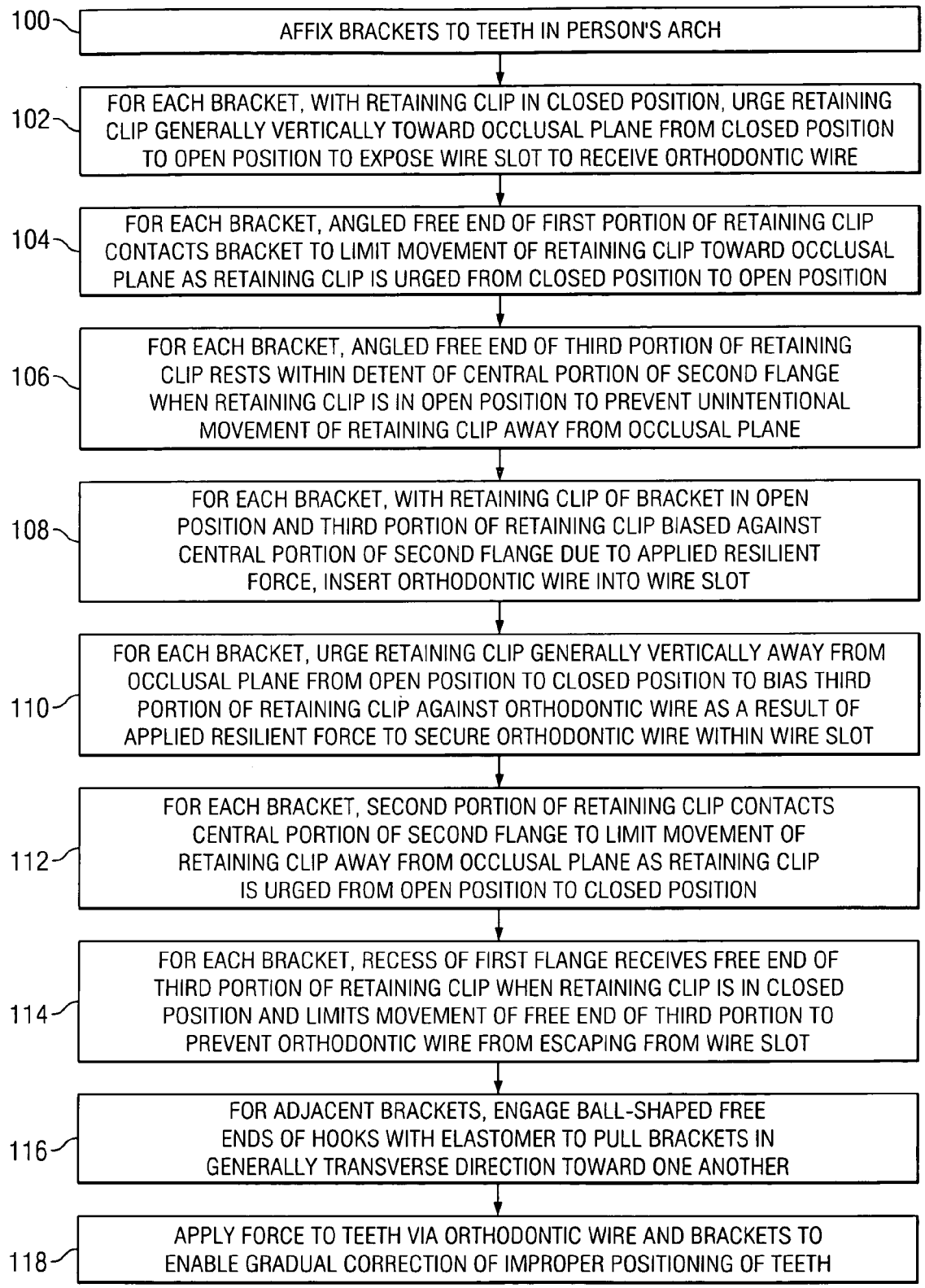
FIG. 18 illustrates an example method of treating an orthodontic patient using a number of self-ligating lingual orthodontic brackets.

FIG. 18 illustrates an example method of treating an orthodontic patient using self-ligating lingual orthodontic brackets 12. Although the method is described as involving brackets 12*a*, 12*b*, 12*c*, or any combination of these, those skilled in the art will appreciate that an analogous method may be performed involving brackets 12*d* (i.e. "reverse brackets"). At step 100, brackets 12 are affixed to at least some teeth in a person's arch, the upper arch for example.

At step 102, for each bracket 12, with retaining clip 32 in the closed position, retaining clip 32 is urged generally vertically toward the occlusal plane from the closed position to the open position to expose wire slot 28 to receive orthodontic wire 14. For example, retaining clip 32 may be urged using an appropriate tool inserted into a notch 42 or in any other manner. At step 104, in certain embodiments, for each bracket 12, angled free end 42 of first portion 34 of retaining clip 32 contacts bracket 12 to limit movement of retaining clip 32 toward the occlusal plane as retaining clip 32 is urged from closed position to open position. At step 106, in certain embodiments, for each bracket 12, angled free end 44 of third portion 38 of retaining clip 32 rests within detent 46 of the central portion of second flange 26 when retaining clip 32 is in the open position to prevent unintentional movement of retaining clip 32 away from the occlusal plane. Of course, if a bracket 12 is already in the open position when that bracket 12 is affixed to a tooth, then steps 102–106 may be eliminated with respect to that bracket 12.

At step 108, for each bracket 12, with retaining clip 32 in the open position and third portion 38 of retaining clip biased against at least the central portion of second flange 26 due to the applied resilient force, orthodontic wire 14 is inserted into wire slot 28 from the lingual side of bracket 12. At step 110, for each bracket 12, retaining clip 32 is urged generally vertically away from the occlusal plane from the open position to the closed position to bias third portion 38 of retaining clip 32 against orthodontic wire 14 as a result of applied resilient force to secure orthodontic wire 14 within wire slot 28. For example, retaining clip 32 may be urged using pressure applied against second portion 36 of retaining clip 32 or in any other manner. At step 112, in certain embodiments, for each bracket 12, second portion 36 of retaining clip 32 contacts the central portion of second flange 36 to limit movement of retaining clip 32 away from the occlusal plane as retaining clip 32 is urged from the open position to the closed position. At step 114, in certain embodiments, for each bracket 12, recess 48 of first flange 24 receives free end 44 of third portion 38 of retaining clip 32 when retaining clip 32 is in the closed position and limits movement of free end 44 of third portion 38 in the generally lingual direction to prevent orthodontic wire 14 from escaping from wire slot 28.

At step 116, in certain embodiments, for one or more pairs of adjacent brackets 12, the ball-shaped free ends of hooks 52 of brackets 12 may be engaged with an elastomer to pull brackets 12 in a generally transverse direction toward one another. At step 118, force is applied to the teeth via orthodontic wire 14 and brackets 12 to enable gradual correction of improper positioning of the teeth.

Particular embodiments of the present invention may provide one or more technical advantages. In particular embodiments, the present invention overcomes difficulties and challenges associated with providing an orthodontic bracket that is self-ligating and also adapted for use inside a person's mouth (i.e. is a lingual bracket). For example, in certain embodiments, the self-ligating lingual brackets must integrate an orthodontic prescription appropriate for self-ligating lingual brackets, including a particular combination of torque, angulation, thickness, or other parameters, that is appropriate for self-ligating lingual brackets and may be substantially different from an orthodontic prescription appropriate for self-ligating labial brackets. As another example, in contrast to self-ligating labial brackets in which the orthodontic wire applies correcting forces against the lingual brackets toward the labial surfaces of the teeth, in certain embodiments the retaining clips and associated structures of the self-ligating lingual brackets must be adapted to accommodate correcting forces that are applied against the retaining clips away from the lingual surfaces of the teeth and may also be stronger than the correcting forces applied in the case of self-ligating labial brackets. As another example, in contrast to self-ligating labial brackets in which retaining clips may be readily accessed from outside the mouth for inserting, securing, and removing the orthodontic wire, in certain embodiments the retaining clips and associated structures of the self-ligating lingual brackets must facilitate access from inside the mouth for inserting, securing, and removing the orthodontic wire. Self-ligating lingual brackets according to certain embodiments of the present invention represent a significant technical advance over the prior art.

Although the present invention has been described above in connection with a number of embodiments, a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A self-ligating lingual orthodontic bracket, comprising:
a base comprising a base surface adapted for coupling to a lingual surface of a tooth in a person's arch;
a first flange extending generally horizontally from the base in a generally lingual direction;
a second flange extending generally vertically from the first flange in a direction generally toward the person's occlusal plane
a third flange extending generally horizontally from the second flange in a generally labial direction, the third flange separated from the first flange generally vertically toward the person's occlusal plane to define a generally transverse wire slot that is exposed from a generally labial direction and adapted to receive an orthodontic wire inserted into the wire slot from the generally labial direction;
a clip slot formed generally vertically through the second flange; and
a flexible retaining clip adapted to secure the orthodontic wire within the wire slot in a self-ligating manner, the retaining clip:
comprising a first portion positioned generally vertically and adapted to move generally vertically within the clip slot toward or away from the occlusal plane, a second portion extending generally horizontally from the first portion in a generally labial direction about at least a central portion of the third flange, and a third portion extending generally vertically from the second portion in a direction generally away from the occlusal plane about at least the central portion of the third flange;
adapted to apply a resilient force to an object positioned between the first and third portions;
adapted to be urged generally vertically toward the occlusal plane from a closed position to an open position to expose the wire slot to receive the orthodontic wire, the third portion being biased against at least the central portion of the third flange when the retaining clip is in the open position due to the applied resilient force; and
adapted to be urged generally vertically away from the occlusal plane from the open position to the closed position to secure the orthodontic wire within the wire slot, the third portion being biased against the orthodontic wire when the retaining clip is in the closed position and the orthodontic wire is secured within the wire slot due to the applied resilient force.

2. The bracket of claim 1, wherein the first portion of the retaining clip comprises an angled free end extending generally vertically out of the clip slot in a direction generally away from the occlusal plane and adapted to contact the bracket to limit movement of the retaining clip toward the occlusal plane as the retaining clip is urged from the closed position to the open position.

3. The bracket of claim 1, wherein the second portion of the retaining clip is adapted to contact the central portion of the third flange to limit movement of the retaining clip away from the occlusal plane as the retaining clip is urged from the open position to the closed position.

4. The bracket of claim 1, wherein:
the central portion of the third flange comprises a detent; and
the third portion of the retaining clip comprises an angled free end adapted to rest within the detent of the central portion of the third flange when the retaining clip is in the open position to prevent unintentional movement of the retaining clip away from the occlusal plane.

5. The bracket of claim 1, wherein the first flange comprises a recess adapted to:
receive a free end of the third portion of the retaining clip when the retaining clip is in the closed position; and
limit movement of the free end of the third portion in a generally labial direction to prevent the orthodontic wire from escaping from the wire slot when the retaining clip is in the closed position.

6. The bracket of claim 1, wherein at least one of the first and third portions of the retaining clip comprises a notch adapted to receive a tool for urging the retaining clip toward the occlusal plane from the closed position to the open position.

7. The bracket of claim 1, wherein the third flange provides a bite plate adapted to contact an occlusal surface of an opposing tooth in the person's opposing arch to limit movement of the tooth toward the opposing tooth.

8. The bracket of claim 1, further comprising a hook extending from a side of the first flange in a direction generally away from the occlusal plane, the hook comprising a ball-shaped free end adapted to engage with an elastomer operable to pull the bracket in a generally transverse direction toward an adjacent bracket.

9. The bracket of claim 1, wherein the tooth is an upper tooth in the person's upper arch and the retaining clip is adapted to be urged generally down into the open position and generally up into the closed position.

10. The bracket of claim 1, wherein the orthodontic wire may have either a circular cross-section or a rectangular cross-section.

11. The bracket of claim 1, wherein the wire slot and retaining clip are adapted to accommodate any of a plurality of orthodontic wires with different cross-sectional dimensions.

12. A method of using self-ligating lingual orthodontic brackets to correct improper positioning of a person's teeth, comprising:
affixing self-ligating lingual orthodontic brackets to teeth in a person's arch, each bracket comprising:
a base comprising a base surface adapted for coupling to a lingual surface of a tooth in a person's arch;
a first flange extending generally horizontally from the base in a generally lingual direction;
a second flange extending generally vertically from the first flange in a direction generally toward the person's occlusal plane
a third flange extending generally horizontally from the second flange in a generally labial direction, the third flange separated from the first flange generally vertically toward the person's occlusal plane to define a generally transverse wire slot that is exposed from a generally labial direction and adapted to receive an orthodontic wire inserted into the wire slot from the generally labial direction;
a clip slot formed generally vertically through the second flange; and
a flexible retaining clip adapted to secure the orthodontic wire within the wire slot in a self-ligating manner, the retaining clip:
comprising a first portion positioned generally vertically and adapted to move generally vertically within the clip slot toward or away from the occlusal plane, a second portion extending generally horizontally from the first portion in a generally labial direction about at least a central portion of the third flange, and a third portion extending generally vertically from the second portion in a direction generally away from the occlusal plane about at least the central portion of the third flange;

adapted to apply a resilient force to an object positioned between the first and third portions;

adapted to be urged generally vertically toward the occlusal plane from a closed position to an open position to expose the wire slot to receive the orthodontic wire, the third portion being biased against at least the central portion of the third flange when the retaining clip is in the open position due to the applied resilient force; and adapted to be urged generally vertically away from the occlusal plane from the open position to the closed position to secure the orthodontic wire within the wire slot, the third portion being biased against the orthodontic wire when the retaining clip is in the closed position and the orthodontic wire is secured within the wire slot due to the applied resilient force;

for each bracket, with the retaining clip of the bracket in the open position and the third portion of the retaining clip biased against at least the central portion of the third flange due to the applied resilient force, inserting an orthodontic wire into the wire slot from the labial side of the bracket;

for each bracket, urging the retaining clip of the bracket generally vertically away from the occlusal plane from the open position to the closed position to bias the third portion of the retaining clip against the orthodontic wire as a result of the applied resilient force to secure the orthodontic wire within the wire slot of the bracket; and applying force to the teeth via the orthodontic wire and brackets to enable gradual correction of the improper positioning of the teeth.

13. The method of claim 12, wherein:

the method further comprises urging the retaining clip generally vertically toward the occlusal plane from a closed position to an open position to expose the wire slot to receive the orthodontic wire;

the first portion of the retaining clip comprises an angled free end extending generally vertically out of the clip slot in a direction generally away from the occlusal plane; and the angled free end of the first portion of the retaining clip contacts the bracket to limit movement of the retaining clip toward the occlusal plane as the retaining clip is urged from the closed position to the open position.

14. The method of claim 12, wherein the second portion of the retaining clip contacts the central portion of the third flange to limit movement of the retaining clip away from the occlusal plane as the retaining clip is urged from the open position to the closed position.

15. The method of claim 12, wherein:

the central portion of the third flange comprises a detent; and the third portion of the retaining clip comprises an angled free end that rests within the detent of the central portion of the third flange when the retaining clip is in the open position to prevent unintentional movement of the retaining clip away from the occlusal plane.

16. The method of claim 12, wherein the first flange comprises a recess that receives a free end of the third portion of the retaining clip when the retaining clip is in the closed position and limits movement of the free end of the third portion in a generally labial direction to prevent the orthodontic wire from escaping from the wire slot when the retaining clip is in the closed position.

17. The method of claim 12, further comprising inserting a tool into a notch in one of the first and third portions of the retaining clip to urge the retaining clip toward the occlusal plane from the closed position to the open position.

18. The method of claim 12, wherein the third flange provides a bite plate that contacts an occlusal surface of an opposing tooth in the person's opposing arch to limit movement of the tooth toward the opposing tooth.

19. The method of claim 12, wherein:

the bracket further comprises a hook extending from a side of the first flange in a direction generally away from the occlusal plane; and the method further comprises engaging a ball-shaped free end of the hook with an elastomer to pull the bracket in a generally transverse direction toward an adjacent bracket.

20. The method of claim 12, wherein the tooth is an upper tooth in the person's upper arch and the retaining clip is urged generally up into the closed position.

* * * * *